United States Patent
Bagwell et al.

(10) Patent No.: US 8,795,236 B2
(45) Date of Patent: Aug. 5, 2014

(54) ONE STEP CECOSTOMY

(75) Inventors: Alison S. Bagwell, Alpharetta, GA (US); Thomas G. Estes, Bonifay, FL (US); Shawn R. Feaster, Waunakee, WI (US); Emily A. Reichart, Atlanta, GA (US); Phillip A. Schorr, Cumming, GA (US); Jennifer S. Stadelman, Alpharetta, GA (US); Kok-Ming Tai, Lawrenceville, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/247,249

(22) Filed: Sep. 28, 2011

(65) Prior Publication Data

US 2013/0079712 A1 Mar. 28, 2013

(51) Int. Cl.
| | |
|---|---|
| *A61M 5/00* | (2006.01) |
| *A61M 29/00* | (2006.01) |
| *A61F 5/445* | (2006.01) |
| *A61M 39/02* | (2006.01) |
| *A61J 15/00* | (2006.01) |
| *A61F 5/442* | (2006.01) |

(52) U.S. Cl.
CPC ........ *A61F 5/445* (2013.01); *A61M 2039/0297* (2013.01); *A61J 15/0065* (2013.01); *A61M 2210/1064* (2013.01); *A61M 2039/0255* (2013.01); *A61M 2039/0282* (2013.01); *A61M 39/0247* (2013.01); *A61J 15/0038* (2013.01); *A61M 2039/0261* (2013.01); *A61F 5/442* (2013.01); *A61F 2005/4455* (2013.01); *A61F 15/0023* (2013.01); *A61J 15/0069* (2013.01); *A61J 15/0042* (2013.01); *A61J 15/0073* (2013.01); *A61J 15/0057* (2013.01); *A61M 2039/0291* (2013.01)

USPC ....................................... 604/175; 604/102.03

(58) Field of Classification Search
USPC .............................. 604/96.01, 99.04, 103.05, 604/103.01–103.03, 175, 102.01, 102.03
See application file for complete search history.

(56) References Cited

U.S. PATENT DOCUMENTS

| | | | |
|---|---|---|---|
| 4,601,713 A * | 7/1986 | Fuqua | 604/514 |
| 5,578,031 A | 11/1996 | Wilk et al. | |
| 6,223,070 B1 | 4/2001 | Chait | |
| 7,070,587 B2 * | 7/2006 | Meier et al. | 604/533 |
| 7,553,273 B2 | 6/2009 | Ferguson et al. | |
| 7,704,203 B2 | 4/2010 | Silverman et al. | |
| 7,758,497 B2 | 7/2010 | Hem | |
| 2001/0016724 A1 * | 8/2001 | Davis et al. | 604/509 |

(Continued)

FOREIGN PATENT DOCUMENTS

EP 1 632 201 A1 3/2006

*Primary Examiner* — Nathan R Price
(74) *Attorney, Agent, or Firm* — James B. Robinson

(57) ABSTRACT

The present disclosure describes a cecostomy tube having a head with an opening and a valve. There is a flexible catheter with a lumen having proximal and distal ends, the proximal end of the catheter in fluid communication with the opening in the head, a portion of the catheter extending away from the head to define the distal end. The catheter also has walls defining inside and outside surfaces from the opening defined in the head to the distal end of the catheter. There is a retainer provided on the distal end of the catheter. The retainer can change shape from a first profile or configuration to a second profile where the second profile is larger than the first profile and the second profile is adapted to retain the cecostomy tube in place in a body. The device may be placed in a single, initial surgical operation.

18 Claims, 6 Drawing Sheets

(56) References Cited

U.S. PATENT DOCUMENTS

| | | |
|---|---|---|
| 2002/0077611 A1 | 6/2002 | Von Dyck et al. |
| 2003/0229332 A1* | 12/2003 | Intoccia ................. 604/508 |
| 2005/0187524 A1 | 8/2005 | Willis et al. |
| 2006/0124126 A1* | 6/2006 | Tanaka .................. 128/200.26 |
| 2007/0016172 A1 | 1/2007 | Charukhchian |
| 2007/0197958 A1 | 8/2007 | Hern |
| 2008/0004487 A1 | 1/2008 | Haverfield |
| 2010/0081991 A1 | 4/2010 | Swisher |
| 2010/0099944 A1 | 4/2010 | Shalon et al. |
| 2010/0204707 A1 | 8/2010 | Tanaka et al. |

* cited by examiner

ONE STEP CECOSTOMY

BACKGROUND

The present disclosure relates to an apparatus and method for performing a cecostomy.

A cecostomy is the placement of a catheter into the cecum of a patient. The cecum is part of the large intestines and located immediately after the small intestine. Patients with fecal incontinence can use a cecostomy tube to administer an enema to quickly and completely evacuate the large intestines from the upper portion of the large intestine to the rectum. This method of delivering an enema (antegrade) is more effective than a retrograde enema since administration of a retrograde enema often involves substantial leakage. A cecostomy clearly improves the quality of life for those suffering chronic fecal incontinence.

Fecal incontinence can be associated with disorders of peristalsis, sensation, sphincter control, anatomy or psychosocial issues. Among the many is etiologies are myelomeningocele, cloacal anomalies, caudal regression syndrome, paraplegia, paralysis, cerebral palsy, and disorders of intestinal motility. Traditional treatments include dietary modification, laxatives, suppositories, enemas, manual dis-impaction, biofeedback and electro-stimulation. Despite these efforts, many patients do not achieve fecal continence and continue to have bowel accidents. Severe fecal incontinence, particularly among children, can result in severe constipation and leakage of fluid from the anus, a source of embarrassment for the child.

A surgically created cecostomy carries risks of stomal stenosis (10 to 33 percent), stomal leakage, appendiceal necrosis, general anesthesia and bowel perforation, but has been found to be an appropriate solution for many patients.

The current method of performing a cecostomy is a two-step process. The procedure requires the inflation of the colon with air until the cecum is distended. A small needle is inserted through the skin into the cecum, and then the surgeon attaches the cecum to the abdominal wall with stitches. A catheter is then threaded into the cecum in place of the needle. To confirm proper placement of the catheter, contrast dye is usually injected through the catheter, using fluoroscopy to make sure the dye travels into the cecum. This initial cecostomy is allowed to heal for about 6 weeks in order to form a stable stoma. Once it is determined that the stoma has healed properly, the initial placement is followed with the placement of a final cecostomy catheter.

One final prior art cecostomy catheter, as shown in FIG. 1, has a low profile "trapdoor" flange fitting 2, designed to lay flat against the skin when not in use, for enhanced patient compliance. This device is described in detail in U.S. Pat. No. 6,223,070 to Dr. Peter Chait. Dr. Chait's device does not use a separate retention element but has helical coils 4 that reform within the intestinal cavity upon the removal of a stiffener (not shown) that is used to insert it. The coils 4 serve as a retaining mechanism that hold the trapdoor flange 2 against the skin 6 of the patient and keep the catheter from simply falling out of the stoma. Since is there are a plurality of coils, it can adjust to varying distances from the skin 6 to the internal intestinal cavity 8.

The Chait Trapdoor™ Cecostomy Catheter is percutaneously inserted through an existing mature tract, created as described above. Once the initial catheter is removed (over a guide wire) a metal stiffener is inserted into the Chait Trapdoor™ Cecostomy Catheter to straighten the coils and to assist in pushing the catheter through the tract over the pre-positioned guide wire. Once the cecostomy catheter is inserted, the stiffener is removed until the Trapdoor™ flange is flush with the skin at the access site. When the stiffener and guide wire are removed, the extra catheter coils will re-form within the cecum, holding the cecostomy catheter in place.

While the prior art procedure has helped many patients struggling with fecal incontinence to lead more normal lives, the requirement for two separate surgeries creates two potential incidents of infection and other complications. In addition, the helical coils can become plugged after some time and so the cecostomy catheter must be replaced from time to time. Lastly, the Chait catheter can sometimes leak when the catheter is not in use.

What is needed is a device for the administration of an antegrade enema that may be inserted into the cecum in a single step, not requiring a primary and secondary surgical operation. This device should also be simple to operate and effectively allow the patient to control the conditions surrounding the administration of an enema. The device should not need to be replaced on a regular basis because of clogging and should minimize leakage outside of the body when not in use.

SUMMARY

The present disclosure describes a device for administering an antegrade enema that may be installed in a surgical operation. The device meets the needs discussed above by allowing placement in a single, initial surgical operation. The device has a different retention system than that of the Chait device that makes clogging of the tube much less likely. The device has a valve, desirably a one-way valve, to reduce or eliminate leakage outside of the body when the device is not in is use.

The device is a cecostomy tube having a head with an opening therethrough with a valve. There is a flexible catheter with a lumen and having a proximal end and a distal end, the proximal end of the catheter in fluid communication with the opening in the head, a portion of the catheter extending away from the head to define the distal end. The catheter also has walls defining inside and outside surfaces from the opening defined in the head to the distal end of the catheter.

There is a retainer provided on the distal end of the catheter. The retainer can change shape from a first profile or configuration to a second profile where the second profile is larger than said first profile and the second profile is adapted to retain the cecostomy tube in place in a body. In the first, compact profile, the retainer may be more easily inserted through the stoma and into the cecum. Once in the cecum, the retainer profile may be changed from the first to the second profile by a number of different means; by dissolving or removing a coating or enveloping layer that holds the retainer in a compacted state, by inflating a balloon or by unfurling an umbrella-like structure.

The cecostomy tube can have a second lumen adapted to deliver fluid from the head to the catheter outside surface. The fluid may be an adhesive that is delivered to the outside surface of the catheter to help bind the cecum to the inner abdominal wall to help create a stable stoma. The adhesive, if used, should be a monomer that polymerizes in the presence of a polar species such as water or protein molecules. Adhering the cecum to the abdominal wall in this manner obviates the need for stitching the two together, although stitches may also be used if desired.

The valve may desirably be a one-way valve like a flapper valve or a duckbill valve.

Also provided herein is a method of performing a cecostomy. The method has the steps of moving the cecum into a position adjacent an inner surface of an abdominal wall, creating a stoma from an outside of an abdomen, through the abdominal wall and into the cecum, inserting a distal end of a cecostomy tube having a retainer through the stoma, and then changing the profile of the retainer on the distal end of the cecostomy tube to a second, larger configuration after the retainer is in the cecum. The cecostomy tube may be installed in a single, initial surgical operation.

The method may further include the step of injecting an adhesive between said cecum and the abdomen from a second lumen in the cecostomy tube.

Other objects, advantages and applications of the present disclosure will be made clear by the following detailed description of a preferred embodiment of the disclosure and the accompanying drawings wherein reference numerals refer to like or equivalent structures.

BRIEF DESCRIPTION OF THE DRAWINGS

In FIG. 5A the retainer is in an expanded configuration.

DETAILED DESCRIPTION

Reference will now be made to the drawings in which the various elements of the present disclosure will be given numeral designations and in which the disclosure will be discussed so as to enable one skilled in the art to make and use the disclosure. It is to be understood that the following description is only exemplary of the principles of the present disclosure, and should not be viewed as narrowing the pending claims. Those skilled in the art will appreciate that aspects of the various embodiments discussed may be interchanged and modified without departing from the scope and spirit of the disclosure.

The cecum in the uppermost part of the lower intestine, located immediately downstream of the small intestine. A cecostomy is the provision of an access from the exterior of the body into the cecum. A cecostomy allows the administration of an antegrade enema to those suffering from fecal incontinence, improving their quality of life and allowing them to more easily control this vital bodily function. This issue impacts many people, including those afflicted by spina bifida and, increasingly, those suffering injuries in so called "extreme sports".

In order to install a cecostomy tube the cecum 20 must be brought into close contact with the inner abdominal wall 22.

Figure 1:
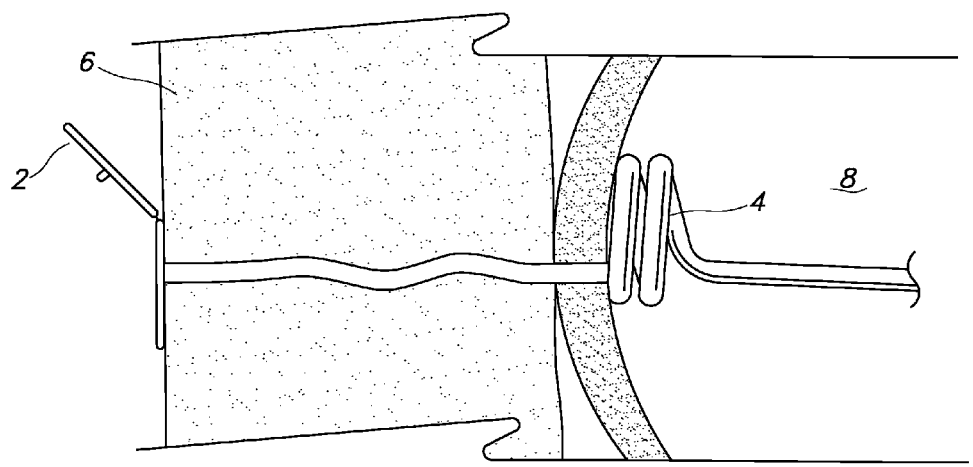
FIG. 1 is a view of a prior art device, a Chait Trapdoor™ Cecostomy Catheter, installed through the skin to the intestinal cavity, and which may be used to administer an enema to the cecum through the "trapdoor" on the surface of the skin (far left in drawing).
Figure 2A:
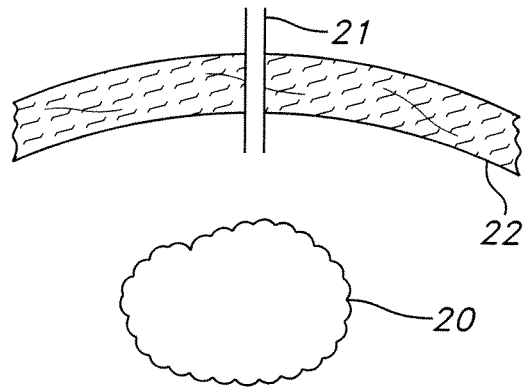
FIGS. 2A, 2B and 2C show a series of views of the movement of the cecum and attachment to the abdominal wall.
Figure 2B:
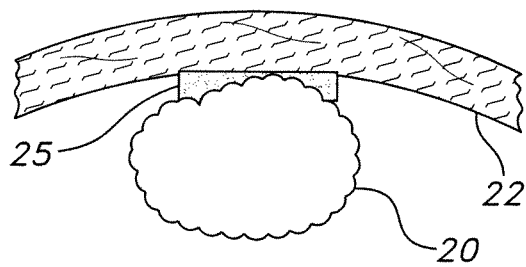
Figure 2C:
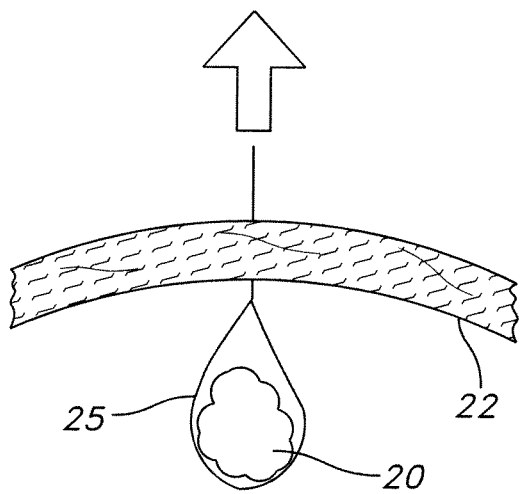

FIGS. 2A, 2B and 2C show a series of views of the movement of the cecum 20 and attachment to the abdominal wall 22. This may be done by first insuflating the cecum with air using a catheter inserted through the rectum. Once the cecum is distended it may be held in this state by the inflation of a balloon in the cecum if desired. When the cecum is in close proximity to the abdominal wall, an initial puncture is made through the abdominal wall using a needle 21, to create a stoma. A guide wire may be installed if desired but is not required. The distal end of the disclosed cecostomy tube is inserted through the skin and into the cecum. It may be inserted over the guidewire if used. As discussed in greater detail below, glue 25 may be injected between the cecum 20 and abdominal wall 22 to hold the cecum 20 in that position.

In an alternative procedure, the abdomen may be pierced with a needle and a "J" shaped hook 23 may be inserted through the abdomen and used to partially wrap around and hook the cecem 20 (FIG. 2C). The cecum 29 may then be drawn toward the abdominal wall 22 by moving the hook toward the abdominal wall. A needle may be inserted to initially puncture the cecum from outside of the abdominal wall to create a stoma.

Figure 3:
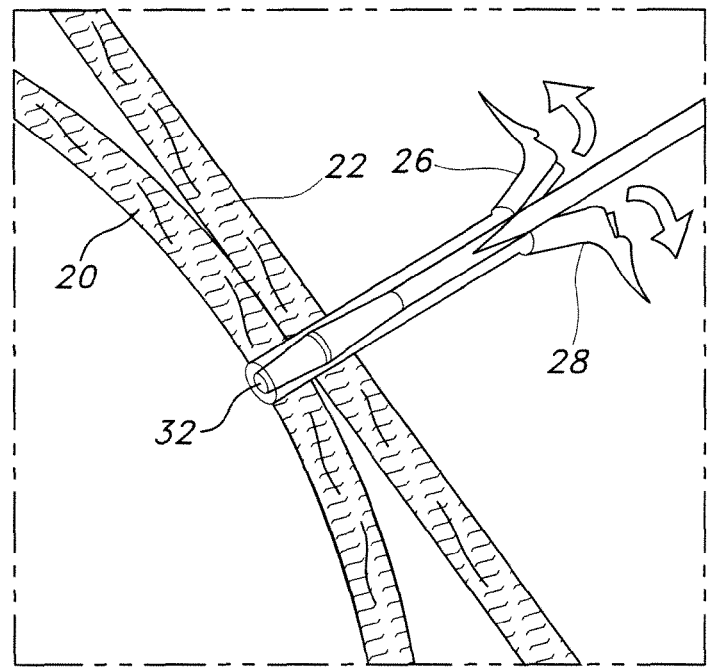
FIG. 3 is a drawing of a peel away dilator that may be used with the disclosed cecostomy tube.
Figure 4:
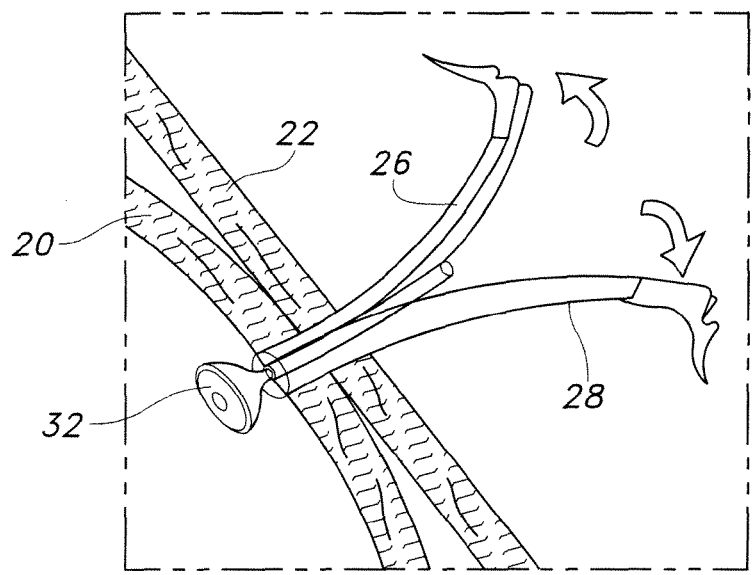
FIG. 4 is another drawing of the peel away dilator that may be used with the disclosed cecostomy tube.

Prior to the insertion of the cecostomy tube into the stoma, a dilator or series of conventional dilators may be used to enlarge the stoma, as desired by the surgeon. Alternatively, a "peel away" dilator 24 may be used. This dilator, as shown in FIGS. 3 and 4, encloses the retainer 32 and the distal part of the cecostomy tube (not visible) between two halves 26, 28. The dilator 24 is inserted into the stoma with the cecostomy tube inside and once the tube is in the desired position, the dilator may be peeled apart as shown by the direction of the arrows in the Figures. The peel-away dilator sheath is separated and removed from the stoma tract and the retainer on the distal, in-dwelling end of the cecostomy tube is unfurled.

Figures 5A, 5B:
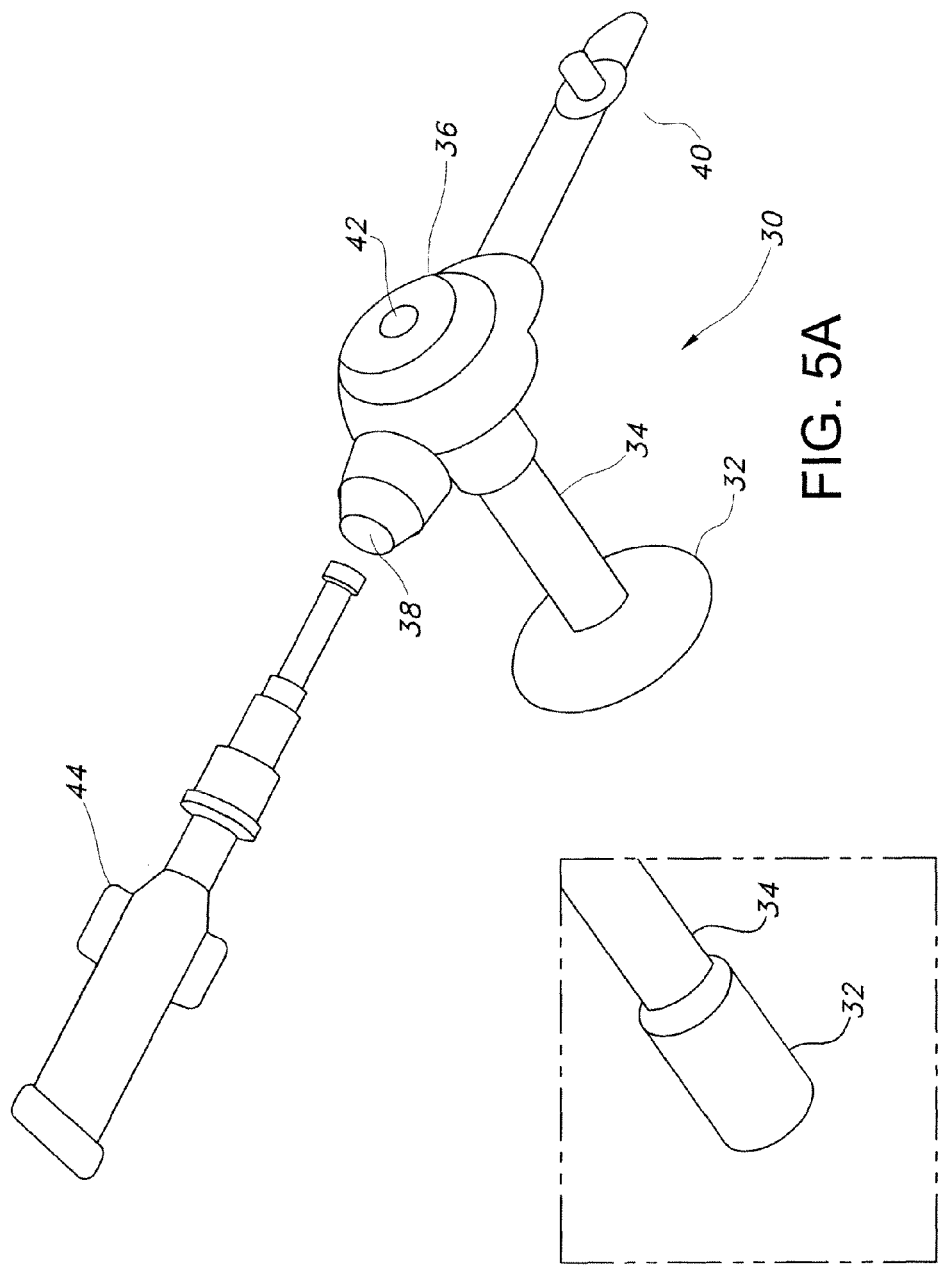
FIG. 5A is a drawing of a cecostomy tube showing a head designed to remain outside the body, a retainer designed to help retain the tube in position, and a shaft or catheter tube connecting the head and retainer.
In FIG. 5B the retainer is in a compressed is configuration.

Turning to FIG. 5B, it can be seen that the distal end of the disclosed cecostomy tube 30 is designed to have a small profile for insertion into the cecum through the abdominal wall. FIG. 5B is a drawing of the distal end of the cecostomy tube 30 showing the retainer 32 on the distal end of the shaft 34 prior to insertion. In one embodiment, the retainer 32 is covered in a coating that envelopes it and keeps it in a small, tightly wound, compacted or folded first profile or configuration around the shaft 34. To install the tube 30, the retainer 32 and shaft 34 are inserted into the stoma that was made into the abdominal wall and cecum, as described above. Once the tube is in position, with the distal end of the shaft 34 carrying the retainer 32 in the cecum, the coating on the retainer 32 dissolves, allowing the retainer 32 on the distal end of the shaft 34 of the tube 30 to expand into a second profile or configuration as it is shown in FIG. 3A. This expansion of the retainer 32 on the distal end of the tube 30 acts as an anchor for the tube 30 and keeps the tube 30 in place within the cecum.

The coating that may be used is one that will dissolve within the body and be harmlessly absorbed or disposed of. The coating or outer shell of a gel capsule, like that used to administer medicine, has been found to work well. In one embodiment, the retainer is folded together to make it very compact and small and then inserted into a pre-formed gelatin capsule. The capsule holds the retainer in this compact, folded configuration until the tube is inserted into the body, whereupon contact with bodily fluids causes the gelatin to dissolve and allows the retainer to unfurl to its fully extended shape. Alternatively, a saline or other solution may be injected into the lumen of the shaft into the cecum to help dissolve the gelatin coating on the retainer, if contact with bodily fluids alone is not sufficiently rapid. A rapid injection of air may also be judiciously used to force the gelatin capsule off of the compacted retainer.

It is also possible to form the capsule in place on a pre-compacted retainer. In this case the retainer may be folded together and held in a compacted configuration by mechanical means. A gelatin composition may be sprayed, dripped or otherwise coated onto the compacted retainer and allowed to solidify. The mechanical means for holding the retainer in the compacted configuration may be carefully removed, allowing the gelatin to hold the retainer in the compacted configuration until it is inserted into the body.

Figure 6A:
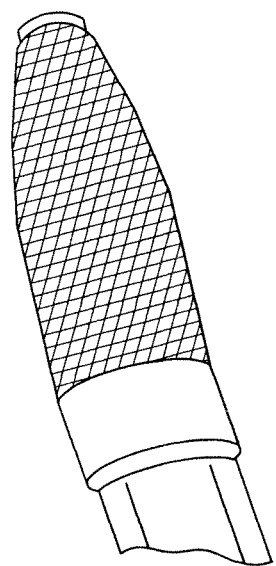
FIGS. 6A and 6B show a cecostomy tube having an umbrella-like design for the retainer.
Figure 6B:
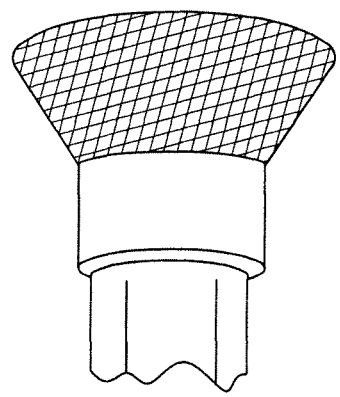

Alternative configurations for the retainer may be used. For example, an umbrella-like unfolding of an anchor 50 as shown in FIGS. 6A and 6B may be used. The retainer alternates between: (a) an insertion/removal state or configuration of a first length such that struts and/or other elements of the retainer are substantially axially aligned with the exterior of the catheter to give an effective cross-sectional area that is substantially the same as that of the catheter, and (b) a deployed state with a second length that is shorter than the first length in which the struts and/or other elements of the retainer have a deployed effective cross-sectional area with a diameter that is substantially greater than that of the catheter. One embodiment of the retainer may include a sleeve that has two opposing ends and may comprise a plastic mesh material such as PET (polyethylene terephthatlate), PEEK (polyether ether ketone) or Nylon (various polyamides). A substantial portion of the exterior surface of the retainer may be covered in a flexible skin that allows unencumbered changes in retainer shapes and states as desired. The skin should not allow in-growth of tissue, be impermeable to liquid, and be substantially not inherently stretchable. This skin may be attached at or towards each opposing end of the retainer to envelop at least a substantial portion of the retainer but not to embed within it. The skin may snugly conform to the retainer in the deployed state. The skin prevents liquid from passing from the exterior of the retainer through the retainer.

Figure 7:
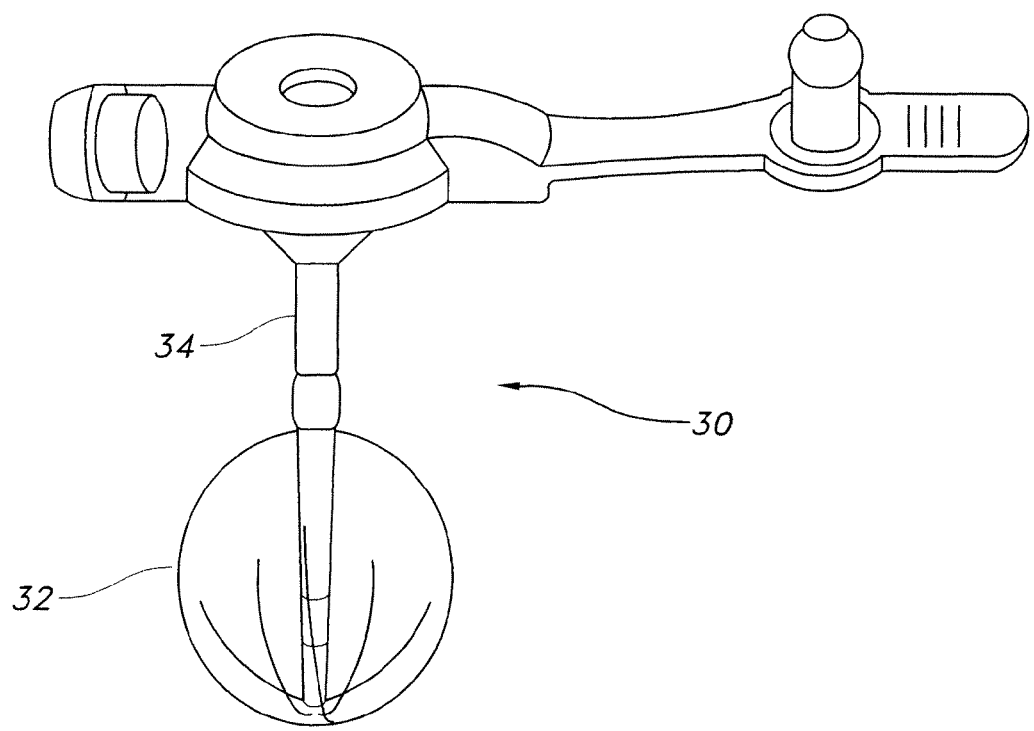
FIG. 7 is a drawing of a cecostomy tube having an inflatable balloon as the retainer, wherein the cecostomy tube is inserted while the balloon is in the un-inflated state and subsequently inflated to help keep the tube in place.

Other means of holding the retainer or anchor closed may also be used. These include mechanical ties or wraps holding the anchor in a closed position that may be removed after installation. The expansion of the anchor may be triggered electrically or magnetically after installation of the tube as well. Still another configuration of the retainer is shown in FIG. 7 which shows the retainer as an inflatable balloon. The shaft 34 having the balloon in the un-inflated state may be inserted through the stoma as described previously and the balloon inflated after it is in the cecum. A separate inflation lumen for the balloon is required.

In still another embodiment, the balloon retainer described immediately above may contain a foam, such as a polyurethane foam which is desirably open celled. The foam may be collapsed by removing air from the balloon. In the collapsed configuration, the retainer is very small and the shaft having the balloon may be inserted in the body through the stoma. Air may be allowed to re-enter the balloon passively after insertion to allow the foam to expand to approximately its original size. Alternatively, the balloon may be affirmatively expanded by injecting air, again causing the foam to expand and substantially fill the balloon interior. The benefit of including a foam in the balloon and not relying on air alone to retain the shape is that, in the case of a leak in the balloon, the foam will remain in place and retain the tube in the proper position. A balloon with air alone could deflate and allow the tube to fall out of or be accidentally removed from the stoma.

After the cecostomy tube 30 is inserted or after the cecum is in close contact with the abdominal wall, a surgical sealant, adhesive or glue may be injected between the two. This adhesive dries quickly and once the adhesive has dried, the cecum and inner abdominal wall are held firmly together without the use of sutures. The adhesive should last for the six week period that is believed to be needed for the stoma to stabilize and remain in place. After six weeks, it is believed that the adhesive will be absorbed by and disposed of by the body. The use of adhesive is optional, however, as some surgeons may not believe it to be necessary considering the size and stability of the retainer, which by itself may be sufficient to hold the cecum against the abdominal wall for six weeks until the stoma matures and is stable.

The adhesive may be injected through a lumen located along the outside, inside or in the wall of the cecostomy tube 30. The distal end of the shaft 34 has at least one outlet port, and desirably a plurality of outlet ports located on the outside surface of the cecostomy catheter or shaft 34 for the adhesive so that it is distributed around and over the length of the shaft 34. FIG. 5A shows a adhesive dispenser 44 that may be used to inject adhesive into lumen 38. Lumen 38 is in fluid communication with the outside of the shaft 34 through at least one port (not shown).

Adhesives that are suitable for use in this application are those that contain monomeric units that polymerize in situ to from a polymeric film. Cyanoacrylate sealants containing alkyl cyanoacrylate monomer are an example of this type, wherein the monomer polymerizes in the presence of a polar species such as water or protein molecules to form an acrylic film. Solvent-based adhesives would be inappropriate in this application since they operate using the principle of evaporation of the solvent, which of course would not function within the body.

One suitable adhesive is available in a skin sealant composition commercially known as InteguSeal® and is available from Medlogic Global, Ltd of Plymouth, England. InteguSeal® skin sealant contains medical grade n-butyl cyanoacrylate monomer (80% w/w). Medical grade cyanoacrylate is double distilled. Non-medical grade cyanoacrylate, in contrast, is single distilled and is typically marketed as a "super adhesive" type adhesive for gluing a wide variety of substrates together. Another film former is Hard as Nails® tosylamide/formaldehyde resin (Del Laboratories Inc., Uniondale N.Y.). Still another suitable adhesive is marketed as a wound closure adhesive under the tradename LiquiBand® by Medlogic.

Once the cecum has been attached to the inside surface of the abdominal wall, the adhesive holding it in position has cured, and the retainer has expanded in the cecum, the installation of the cecostomy tube is complete. No subsequent medical procedure is normally needed. It is possible however that the materials from which the cecostomy device are made may deteriorate over time. In such a case the cecostomy device may be removed and replaced.

In order to introduce an antegrade enema, the closure fob 40 (if present) is removed from the proximal end or "head" 36 of the cecostomy tube (FIG. 3A) where it is normally bent over and inserted in a manner to keep the opening 42 closed. The enema solution is introduced through the opening 42 into a lumen (not shown) that passes through the shaft or catheter 34 of the tube 30 and terminates in the retainer 32, desirably in the center. The enema solution then exits the retainer 32 into the cecum. There is desirably a valve within the tube 30 located in either the head 36 or shaft 34. This valve is desirably a one-way valve like a duckbill valve. The valve serves to keep the tube 30 from leaking fluid outside the body when the tube is not in use, a problem that has been identified in the prior art and which can cause problems with odor, embarrassment and the staining of clothing.

The lumen in the shaft 34 of the tube 30 that runs from the opening 42 to the retainer 32 is short and straight when compared to the prior art Chait Trapdoor™ device, making it less likely to become clogged. The prior art device, particularly the "pig tail" or coil, makes the prior art device's lumen much longer than that of the disclosed device. In addition, the disclosed tube 30 desirably has a larger diameter lumen than the prior art device, also helping to prevent clogging. The result of the larger diameter and shorter length lumen make it likely that the disclosed device will be able to be retained in the body for an extended time before being replaced due to clogging. The prior art device is normally replaced on a regular schedule, generally annually.

The location of a valve in the tube 30 also helps prevent leakage from the device. The valve may desirably be a one-way flapper or duckbill type valve. Alternatively, but less desirably, the valve may be a twist-type valve that closes when twisted in one direction and opens when twisted in the other direction. Any other valve known to function in this service and known to those skilled in the art may be used.

The dimensions of the disclosed device are approximate since there are varying sizes for different aged and sized individuals. Common catheter or shaft outside dimensions however, are: 12 French (4.0 mm) with a stoma length that could range from 0.8 cm to 4 cm, 14 French (4.7 mm) with a stoma length that could range from 0.8 cm to 5.0 cm, 18 French (6.0 mm) with a stoma length that could range from 0.8 cm to 5.0 cm, 20 French (6.7 mm) with a stoma length that could range from 0.8 cm to 5.0 cm, and 24 French (8.0 mm) with a stoma length that could range from 1.5 cm to 5.0 cm. The retainer desirably has a diameter or width in its fully deployed or unfurled configuration of at least twice the outside diameter of the shaft to which it is attached. It may have a width of at least three times or even four times the diameter of the shaft to which it is attached.

It is also desirable though not required that the cecostomy tube have a coating of an antimicrobial compound in order to help reduce the possibility of infection. Appropriate antimicrobial compounds include silver containing coatings and polysiloxanes. Other such materials as are known to those skilled in the art may also be used.

As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. An cecostomy tube comprising:
   a head, the head defining an opening therethrough;
   the head further defining a valve in the opening;
   a flexible catheter defining a first lumen and having a proximal end and a distal end, the proximal end of the catheter in fluid communication with the opening in the head, a portion of the catheter extending away from the head to define the distal end, the catheter having walls defining inside and outside surfaces from the opening defined in the head to the distal end of the catheter;
   a retainer provided on the distal end of the catheter, said retainer having a first profile and a second profile, said second profile being larger than said first profile and adapted to retain said cecostomy tube in place in a body; and
   a second lumen adapted to deliver adhesive from the head to the catheter outside surface.

2. The cecostomy tube of claim 1 wherein said second lumen can deliver adhesive along the outside surface of said catheter between the head and the retainer.

3. The cecostomy tube of claim 2 wherein said adhesive is a monomer that polymerizes in the presence of a polar species such as water or protein molecules.

4. The cecostomy tube of claim 1 wherein said retainer changes from a first configuration to a second configuration, said first configuration being smaller than said second configuration for insertion of said retainer into the body, said second configuration adapted to retain the cecostomy tube in place in the body.

5. The cecostomy tube of claim 4 wherein said retainer changes from said first configuration to said second configuration in response to contact with fluid.

6. The cecostomy tube of claim 5 wherein said retainer is held in said first profile by a gelatin capsule prior to insertion.

7. The cecostomy tube of claim 5 wherein said retainer is held in said first profile by a gelatin coating prior to insertion.

8. The cecostomy tube of claim 4 wherein said retainer is a balloon.

9. The cecostomy tube of claim 8 wherein said retainer changes from said first configuration to said second configuration by being inflated.

10. The cecostomy tube of claim 8 wherein said balloon contains a foam.

11. The cecostomy tube of claim 2 wherein said second lumen has a plurality of outlet ports located on the outside surface of the cecostomy catheter for the adhesive so that the adhesive is distributed around and over the length of the catheter.

12. The cecostomy tube of claim 1 wherein said valve is a one-way valve selected from the group consisting of flapper valves and duckbill valves.

13. A method of performing a cecostomy, comprising the steps of:
    moving the cecum into a position adjacent an inner surface of an abdominal wall,
    creating a stoma from an outside of an abdomen, through the abdominal wall and into said cecum,
    inserting a distal end of a cecostomy tube through said stoma, said cecostomy tube having:
    a head, the head defining an opening therethrough;
    the head further defining a valve in the opening;
    a flexible catheter defining a first lumen and having a proximal end and a distal end, the proximal end of the catheter in fluid communication with the opening in the head, a portion of the catheter extending away from the head to define the distal end, the catheter having walls defining inside and outside surfaces from the opening defined in the head to the distal end of the catheter; and
    a retainer provided on the distal end of the catheter, wherein the retainer has a first profile and a second profile, said second profile being larger than said first profile and said second profile is adapted to retain said cecostomy tube in place in a body, said first profile adapted to allow insertion of the retainer through the stoma, and wherein said cecostomy tube is installed in a single operation, and injecting an adhesive between said cecum and said abdomen from a second lumen in said cecostomy tube.

14. The method of performing a cecostomy of claim 13 further comprising the steps of stitching the cecum to the abdomen.

15. The method of performing a cecostomy of claim 12 further comprising the step of allowing said retainer to assume said second profile in response to contact with bodily fluids or other liquids.

16. The method of performing a cecostomy of claim 14 wherein said retainer is held in said first profile by a gelatin capsule prior to insertion.

17. The method of performing a cecostomy of claim 14 wherein said retainer is held in said first profile by a gelatin coating prior to insertion.

18. The method of performing a cecostomy of claim 12 wherein said retainer is a balloon.

* * * * *